US012667656B2

(12) United States Patent
Fineout et al.

(10) Patent No.:    US 12,667,656 B2
(45) Date of Patent:        Jun. 30, 2026

(54) SURGICAL IRRIGATION CASSETTE

(71) Applicant: Stryker Corporation, Kalamazoo, MI (US)

(72) Inventors: Ben Fineout, Zeeland, MI (US); Brett Merkel, Portage, MI (US); Jonathan Bodnar, Keller, TX (US); Robert Mitchell Baldwin, Grand Rapids, MI (US); Marc Arthur, Rivers Junction, MI (US); Steve Rolfson, Jr., Kalamazoo, MI (US)

(73) Assignee: Stryker Corporation, Portage, MI (US)

( * ) Notice: Subject to any disclaimer, the term of this patent is extended or adjusted under 35 U.S.C. 154(b) by 1499 days.

(21) Appl. No.: 17/278,755

(22) PCT Filed: Sep. 18, 2019

(86) PCT No.: PCT/US2019/051690
§ 371 (c)(1),
(2) Date: Mar. 23, 2021

(87) PCT Pub. No.: WO2020/068509
PCT Pub. Date: Apr. 2, 2020

(65) Prior Publication Data
US 2022/0031928 A1      Feb. 3, 2022

Related U.S. Application Data

(60) Provisional application No. 62/749,320, filed on Oct. 23, 2018, provisional application No. 62/735,850, filed on Sep. 24, 2018.

(51) Int. Cl.
*A61M 1/00*        (2006.01)

(52) U.S. Cl.
CPC ................ *A61M 1/74* (2021.05); *A61M 1/72* (2021.05); *A61M 1/73* (2021.05); *A61M 1/77* (2021.05);
(Continued)

(58) Field of Classification Search
CPC ...... A61M 1/77; A61M 2205/12; A61M 1/72; A61M 2210/0612; A61M 3/0201;
(Continued)

(56) References Cited

U.S. PATENT DOCUMENTS 5,046,486 A      9/1991  Grulke et al.
5,163,900 A  *  11/1992  Wortrich ............. A61M 3/0201
604/30
(Continued)

FOREIGN PATENT DOCUMENTS

CN        1860297 A      11/2006
CN      102413849 A       4/2012
(Continued)

OTHER PUBLICATIONS

CUSA, "CUSA Clarity Product Information Sheet", https://www.youtube.com/watch?v=MSaCRYmCQYA, Mar. 3, 2017, 1 page.
(Continued)

*Primary Examiner* — Scott J Medway
(74) *Attorney, Agent, or Firm* — Howard & Howard Attorneys PLLC

(57)        ABSTRACT

A surgical irrigation cassette comprises a cassette housing, a portion of a pump, and fluid pathways. The housing defines a chamber therein and a first console connector including a first pneumatic connector port. The pump portion includes an intake side of the pump and an output side of the pump. The fluid pathways are disposed at least in part within the chamber. A first fluid pathway, in an installed position, connects the intake side of the pump with a supply fluid container. A second fluid pathway, in an installed position, connects the output side of the pump and a handpiece. A third fluid pathway, in an installed position, connects the
(Continued)

handpiece and a waste container A fourth fluid pathway, in an installed position, connects the first console connector and the waste container.

24 Claims, 12 Drawing Sheets

(52) U.S. Cl.
CPC ......... *A61M 1/782* (2021.05); *A61M 2205/12* (2013.01); *A61M 2205/128* (2013.01); *A61M 2205/3331* (2013.01)

(58) Field of Classification Search
CPC ............ A61M 1/74; A61M 2205/3331; A61M 2205/123; A61M 1/774; A61M 2205/121; A61M 2205/128; A61M 3/0202; A61M 3/0258; A61M 1/804; A61M 3/022; A61M 2205/50; A61M 1/743; A61M 2205/52; A61M 3/0216; A61F 9/00736; A61F 9/00745; A61F 9/007
See application file for complete search history.

(56) References Cited

U.S. PATENT DOCUMENTS

| | | | |
|---|---|---|---|
| 5,810,766 A | | 9/1998 | Barnitz et al. |
| 5,897,524 A | * | 4/1999 | Wortrich ............... A61M 1/742 |
| | | | 604/30 |
| 6,099,494 A | | 8/2000 | Henniges et al. |
| 6,511,454 B1 | | 1/2003 | Nakao et al. |
| 7,604,607 B2 | | 10/2009 | Cull et al. |
| 7,632,079 B2 | | 12/2009 | Hershberger et al. |
| 9,482,216 B2 | | 11/2016 | Sorensen |
| 9,889,246 B2 | | 2/2018 | Woolford |
| 10,182,940 B2 | | 1/2019 | Chandrakant et al. |
| 2007/0085686 A1 | | 4/2007 | Oz |
| 2008/0114372 A1 | | 5/2008 | Edwards et al. |
| 2009/0163852 A1 | | 6/2009 | Cull |
| 2016/0220751 A1 | * | 8/2016 | Mallough ............... A61M 1/72 |
| 2017/0333606 A1 | * | 11/2017 | Manandhar ........ A61B 1/00135 |
| 2018/0235583 A1 | | 8/2018 | VanderWoude et al. |

FOREIGN PATENT DOCUMENTS

| | | |
|---|---|---|
| CN | 104640523 A | 5/2015 |
| JP | 2010099208 A | 5/2010 |

OTHER PUBLICATIONS

International Search Report for Application No. PCT/US2019/051690 dated Dec. 16, 2019, 4 pages.

Stryker "Sonopet (Showing Pump Arrangement) Information Sheet", 2021, 1 page.

Stryker, "Crossflow, Inflow and Outflow Cassettes Information Sheet", 2019, 1 page.

English language abstract for CN 102413849 A extracted from espacenet.com database on Sep. 27, 2023, 2 pages.

English language abstract and machine-assisted English translation for JP 2010-099208 A extracted from espacenet. com database on Sep. 27, 2023, 17 pages.

English language abstract for CN 1860297 A extracted from espacenet. com database on Jul. 2, 2024, 2 pages.

English language abstract for CN 104640523 A extracted from espacenet.com database on Jul. 2, 2024, 2 pages.

\* cited by examiner

SURGICAL IRRIGATION CASSETTE

RELATED APPLICATIONS

This patent application claims priority to and all the benefits of International Application No. PCT/US2019/051690 filed on Sep. 18, 2019 which claims priority to and all the benefits of both U.S. Provisional Patent Application No. 62/749,320 filed on Oct. 23, 2018 and U.S. Provisional Patent Application No. 62/735,850 filed on Sep. 24, 2018, which are herein incorporated by reference in their entireties.

BACKGROUND

A surgical fluid management system, as may be incorporated into a surgical cutting system, may allow communication of fluid from a fluid source to a surgical site, and from the surgical site to a waste canister, without contaminating an associated vacuum pump or fluid supply pump.

DETAILED DESCRIPTION

Figure 1:
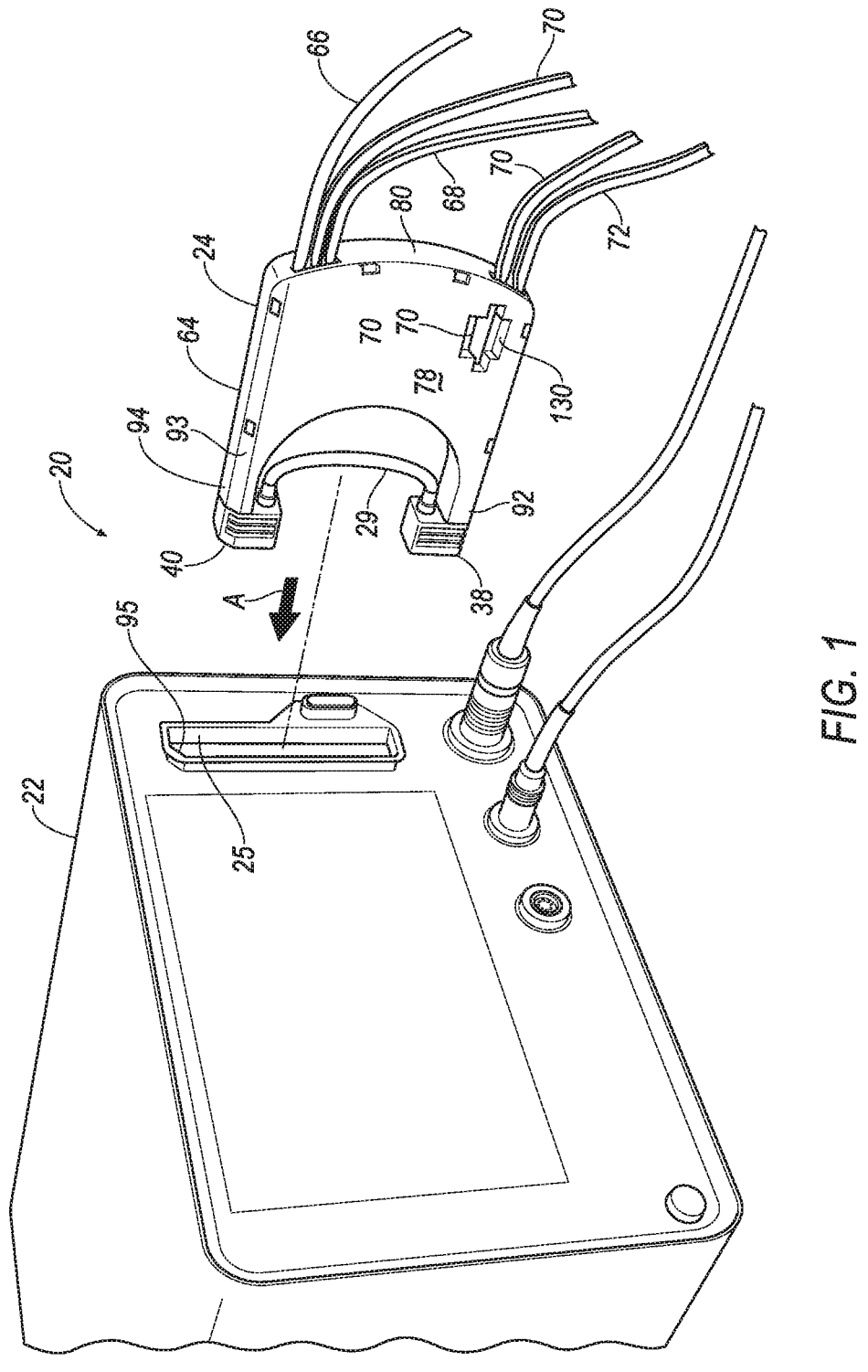
FIG. 1 is a perspective view of an example surgical irrigation cassette positioned for insertion into a control console.

The use of a first cassette to connect a surgical cutting tool to a source of sterile fluid and the use of a second single use cassette to connect the surgical tool to a fluid vacuum are both known. A disclosed single single-use cassette facilitates connecting the surgical tool to each of a vacuum source and a fluid source. The cassette may be a single-use cassette, being disposed of after a single use.

A surgical irrigation cassette comprises a cassette housing, a liquid transfer portion of a pump, and a plurality of fluid pathways. The housing is substantially rigid and defines a chamber therein and a first console connector including a first pneumatic connector port. The liquid transfer portion of a pump includes an intake side of the pump and an output side of the pump. The fluid pathways are disposed at least in part within the chamber, include first, second, third and fourth fluid pathways. The first fluid pathway includes a first end connected with the intake side of the pump, and a second end for connecting with a supply fluid container. The second fluid pathway includes a first end connected with the output side of the pump, and a second end for connecting with a handpiece. The third fluid pathway including a first end for connecting with the handpiece, and a second end for connecting with a waste container. The fourth fluid pathway includes a first end connected with the first console connector and a second end for connecting with the waste container.

The cassette may include a second console connector.

The surgical irrigation cassette may include a fifth fluid pathway. The fifth fluid pathway may include a first end connected with the third fluid pathway, and a second end connected with a second console of the housing.

A fluid management system comprises a console, a vacuum source, a first pressure sensor, a second pressure sensor, and a cassette. The console defines a cassette aperture and has two pneumatic console ports therein. The vacuum source is connected to the console or integrated into the console and is in communication with a first of the pneumatic console ports. The first pressure sensor is integrated into the console and is in communication with a second of the pneumatic console ports. The second pressure sensor is integrated into the console and is in communication with the first of the pneumatic console ports. The cassette is selectively slidably disposed within the cassette aperture. The cassette comprises a housing, a liquid transfer portion of a pump, and a plurality of fluid pathways. The housing is substantially rigid and defining a chamber therein. The liquid transfer portion of a pump includes an intake side of the pump and an output side of the pump. The plurality of fluid pathways includes a first fluid pathway, a second fluid pathway, a third fluid pathway, a fourth fluid pathway and a fifth fluid pathway, each disposed at least in part within the chamber. The first fluid pathway includes a first end connected with the intake side, and a second end for connecting with a supply fluid container. The second fluid pathway includes a first end connected with the output side, and a second end for connecting with a handpiece. The third fluid pathway includes a first end for connecting with the handpiece, and a second end for connecting with a waste container. The fourth fluid pathway includes a first end connected with a first console connector of the housing and a second end for connecting with the waste container. The first console connector has a first pneumatic connector port pneumatically connected with the first of the pneumatic console ports when the cassette is installed in the cassette aperture. The fifth fluid pathway has a first end connected with the third fluid pathway and a second end connected with a second console connector of the housing. The second console connector has a second pneumatic connector port pneumatically connected with the second of the pneumatic console ports when the cassette is installed in the cassette aperture.

The cassette housing may include a first wall and a substantially parallel second wall connected by a peripheral third wall.

The cassette housing may have a substantially C-shaped side defining a first arm and a second arm wherein the first console connector is fixed to the first arm and the second console connector includes a second pneumatic connector port is fixed to one of the first arm and the second arm.

The second console connector may be fixed to the second arm.

Each of the pneumatic connector ports may be defined by an associated aperture for receiving a port tube. The console connectors may further each include a seal for sealing engagement with the port tube.

The console connectors may each include a seal for pneumatic sealing engagement with a pneumatic port tube of a console.

Each console connector may include a bidirectional valve having a closed condition when the console connectors are not in receipt of the pneumatic port tube.

The bidirectional valve may be formed of a polymeric material. The bidirectional valve may include a concave shape from an exterior orientation with slits therethrough.

The the bidirectional valve and the seal may be formed integrally of the polymeric material.

The housing may include a window disposed over a one of the pathways for receiving a path restrictor.

The housing may include a window disposed over the third fluid pathway for receiving a path restrictor.

The cassette may further comprise a liquid stop connector that comprises a reservoir and a normally open one-way valve. The reservoir may be disposed in the housing between the third fluid pathway and the fifth fluid pathway. The one-way valve may be disposed between the third fluid pathway and the reservoir.

The cassette, and more particularly the liquid stop connector, may further comprise a pipe disposed in and comprising part of the third fluid pathway wherein the reservoir is disposed between the pipe and the fifth fluid pathway and the one-way valve is disposed between the pipe and the reservoir.

The one-way valve may comprise a ball-check valve wherein in an installed orientation a ball of the ball-check valve is biased to the open position by gravity and may be forced upward to the closed position by one of impingement of liquid from the third fluid pathway thereagainst and an increase in fluid pressure in the third fluid pathway relative to the fifth fluid pathway.

The reservoir may include an angled floor above the ball-check valve tapering toward the ball-check valve, defining a liquid flow path in the installed orientation from the reservoir to the ball-check valve for flow therepast and into the third fluid pathway in the open position.

The reservoir may include a baffle wall horizontally positioned between the ball-check valve and a connection to the fifth fluid pathway.

The baffle wall may have a lower end defining a liquid-return gap between the baffle wall and the floor and a top end in engagement with a cover of the reservoir.

The cassette may further include a handpiece connector connected to the second end of the second fluid pathway and a first end of the third fluid pathway, the handpiece connector comprising part of each of the second fluid pathway and the third fluid pathway.

The first fluid pathway may include an IV bag connector.

The fourth fluid pathway may include a liquid-blocking filter.

The liquid transfer portion of the pump may comprise a compressible peristaltic pump tube disposed outside of the housing.

Each of the console connectors may include a connector housing and a pneumatic interface sleeve. The connector housing may be substantially rigid and may have a receiving tube that is in engagement with the peristaltic pump tube. The receiving tube may define a part of one of the first fluid pathway and the second fluid pathway. The pneumatic interface sleeve may be formed as part of the connector housing and have an aperture therethrough and a seal disposed in the aperture.

Each console connector may include a bidirectional valve having a closed condition when the cassette is not disposed in a console.

The fluid pathways disposed within the housing may comprise at least in part flexible tubes. The housing may include internal support walls along which the flexible tubes are disposed.

The fluid management system may further comprise the supply fluid container, the handpiece, and the waste container.

A method of using a surgical irrigation cassette comprising the steps of providing the cassette, inserting the cassette into a control console, and connecting the cassette to a supply fluid container, a handpiece and to a waste container. The cassette is provided, with the cassette having each of a housing, a pump tube, and a plurality of fluid pathways. The housing is substantially rigid and defines a chamber therein. The pump tube is a compressible peristaltic pump tube and is disposed outside of the housing. The plurality of fluid pathways is disposed at least in part within the chamber, and includes a first fluid pathway, a second fluid pathway, a third fluid pathway, a fourth fluid pathway and a fifth fluid pathway. The first fluid pathway includes a first end connected with a first end of the pump tube, and a second end for connecting with the supply fluid container. The second fluid pathway includes a first end connected with a second end of the pump tube, and a second end for connecting with the handpiece. The third fluid pathway includes a first end for connecting with the handpiece, and a second end for connecting with the waste container. The fourth fluid pathway includes a first end connected with a first console connector fixed to the housing, and a second end for connecting with the waste container. The fifth fluid pathway has a first end connected with the third fluid pathway, and a second end connected with a second console connector fixed to the housing. The control console into which the cassette is inserted includes or is connected to a vacuum source. The second end of the first fluid pathway is connected to the supply fluid container. The second end of the second fluid pathway is connected to the handpiece. The first end of the third fluid pathway is connected to the handpiece. The second end of the third fluid pathway is connected to the waste container. The second end of the fourth fluid pathway is connected to the waste container.

A pump roller may be selectively engaged with the peristaltic pump tube with such engagement displacing fluid from the supply fluid container to the handpiece. The method may further comprise the step of selectively modulating the vacuum source to regulate a vacuum pressure at the handpiece.

The method may further comprise the steps of providing an aspiration manifold and selectively connecting the fifth fluid pathway to atmosphere through the aspiration manifold. The aspiration manifold may be disposed between the vacuum source and the cassette. The aspiration manifold may be fluidly connected to the vacuum source and to atmosphere and to the console connectors.

The method may further comprise the step of connecting the fifth fluid pathway to atmosphere responsive to an increase in a sensed vacuum magnitude at the handpiece reaching a predetermined threshold.

Relative orientations and directions (by way of example, upper, lower, bottom, rearward, front, rear, back, outboard, inboard, inward, outward, lateral, left, right, proximally, distally) are set forth in this description not as limitations, but for the convenience of the reader in picturing at least one embodiment of the structures described.

The elements shown may take many different forms and include multiple and/or alternate components and facilities. The example components illustrated are not intended to be limiting. Additional or alternative components and/or implementations may be used. Further, the elements shown are not necessarily drawn to scale unless explicitly stated as such.

As illustrated in FIGS. 1 through 14, an example surgical fluid management system 20 includes an example control console 22 and an example removable cassette 24 that may be selectively received by and engaged with the console 22.

FIG. 1 illustrates the cassette 24 disposed outside of the console 22, with the cassette 24 in alignment with a cassette aperture 25, referred to herein as a receiving slot 25, in the console in anticipation of the cassette 24 being moved in the direction of an arrow A for insertion into the slot 25. The receiving aperture 25 need not be limited in shape to a slot, and may have other geometric shapes, including by way of example and not limitation, a circular opening, a square opening, an oval opening, and so on. The cassette 24 may be selectively removably inserted in the console 22 by slidably pushing it into the slot 25. Once inserted in the console 22, the cassette 24 may be considered to be disposed in the console 22. Thus, an inserted cassette 24 is disposed in the console 22. The cassette 24 may be selectively removed from the console 22 by pulling it from the slot 25. Removal may be facilitated by pressing a release button or switch (not shown) prior to or while withdrawing the cassette 24 from the console 22.

Figure 2:
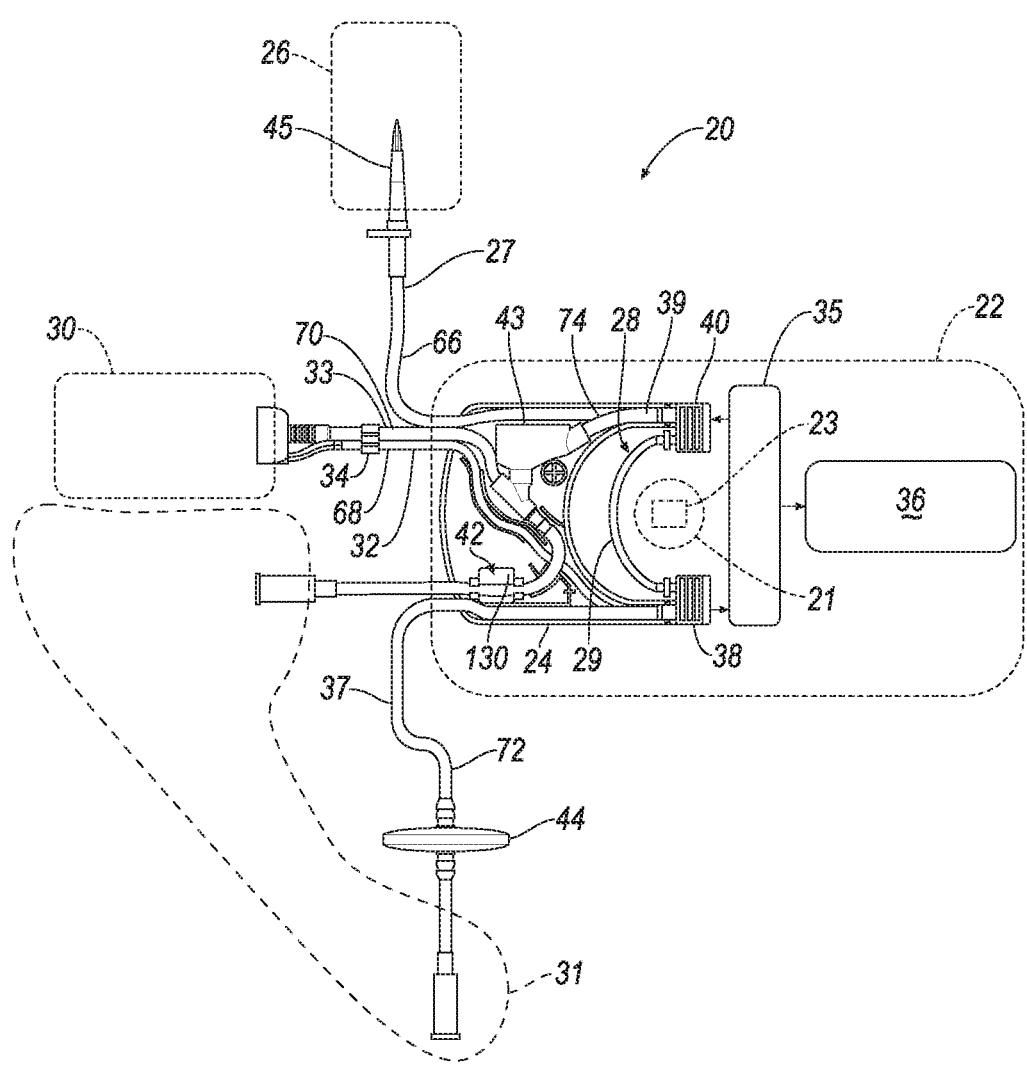
FIG. 2 schematically illustrates an example of a surgical fluid management system and the relationship of the cassette of FIG. 1 with other components of the fluid management system.

FIG. 2 schematically illustrates the relationship of the cassette 24 with other system components. A role of the cassette 24 is to aid in connecting the illustrated components. A plurality of fluid pathways passing through and incorporated into the cassette 24 may connect certain of the system components. The cassette 24 is illustrated as disposed in the console 22.

The cassette 24 is shown as being also connected by a first fluid pathway 27 to a fluid source 26. By way of example, and not limitation, the fluid source 26 may be in the form of a supply fluid container. By way of example, and not limitation, the supply fluid container may be in the form of an intravenous bag 26 with a liquid solution disposed therein. The intravenous bag 26 is also referred to herein as the IV bag 26. The cassette 24 may include an IV bag connector 45 to facilitate coupling with an IV bag 26. The first fluid pathway 27 is connected on a first end to an intake side of a pump 28 that may have a liquid transfer portion incorporated in part in the cassette 24. The pump 28 may be a positive displacement pump. By way of example, and not limitation, one form of positive displacement pump is a peristaltic pump 28 which is described in more detail below. While the pump 28 detailed in this description is the peristaltic pump, other pump types, some of which are identified below, may be employed. The peristaltic pump 28 may incorporate a peristaltic pump tube 29 incorporated into the cassette 24. The peristaltic pump tube 29 may comprise a liquid transfer portion of the pump 28. A pump roller 21 for the pump 28 may be disposed in the console 22 and be driven by a pump motor 23, which also may be disposed in the console 22. The fluid pathway 27 is connected on a second end to the fluid source 26. The liquid solution in the IV bag 26 may be selected for suitability as a surgical site wash. As noted above, alternative pumps may be employed, one example being, without limitation of such alternatives, centrifugal pumps. Yet alternative forms of pumps may be found in U.S. Pat. Nos. 5,046,486 and 6,099,494. Another alternative pump may have a positive displacement pump rotor (not shown) disposed in the cassette serving as the liquid transfer portion of the pump and a drive wheel disposed in the console. The drive wheel (not shown), driven by the motor 23 much like the pump roller 21, may drive the pump rotor without mechanical contact therebetween by establishing a magnetic driving connection between the wheel and the rotor.

The cassette 24 may also be connected to a surgical handpiece 30 by a second fluid pathway 32 and a third fluid pathway 33. The fluid pathways 32, 33 are incorporated at least in part into the cassette 24. An example handpiece 30 is found in the Sonopet® Ultrasonic Aspirator by Stryker®, with Stryker including Stryker Corporation. The handpiece 30 may allow cutting of tissue, fluid supply to the surgical site, and removal by suction of fluid and small bits of debris, more particularly, cutting debris, from the surgical site. Supply of fluid to the surgical site may be alternatively referred to as irrigation of the surgical site. Removal of fluid and removal of debris may be achieved by and alternatively referred to as suction of the same. Suction may be achieved by application of vacuum, described in more detail below. Control of suction and irrigation at the surgical site may be collectively referred to herein as fluid management. The second fluid pathway 32 may supply fluid to the surgical site through the handpiece, and the third fluid pathway 33 may remove fluid from the surgical site via the handpiece 30.

The second fluid pathway 32 includes a first end connected to an output side of the pump 28 and a second end for connecting to the handpiece 30. The third fluid pathway 33 includes a first end for connecting with the handpiece 30 and a second end for connecting with a waste container 31. The waste container 31 may be in the form of a rigid waste canister 31. A handpiece connector 34 may be interposed between the cassette 24 and the handpiece 30 as part of each of the second fluid pathway 32 and the third fluid pathway 33.

The cassette 24 may also be connected to the waste canister 31 by the third fluid pathway 33. The waste canister 31 may receive waste fluid and any accompanying debris that is suctioned from the surgical site by the handpiece 30 via the third fluid pathway 33.

The cassette 24 may also be connected to an aspiration manifold 35 that may be integrated into the console 22. A vacuum source 36, by way of example and not limitation, a vacuum pump, may be selectively pneumatically connected to the cassette 24 via the aspiration manifold 35 and an associated vacuum pressure at the handpiece 30 and in the waste canister 31 being managed by a system operator, inclusive of a surgeon and any other system user, and system control logic within the console 22. The term vacuum pressure as used herein is equivalent to the terms vacuum and negative pressure, all of which are also used herein, all meaning a pressure less than that of a pressure of ambient air. The term ambient air as used herein is equivalent to the term atmosphere, both of which are used herein. The pressure of ambient air is referred to herein as atmospheric pressure. The fourth fluid pathway 37 has a first end connected with a first console connector 38 of the cassette 24 for connecting with the vacuum source 36 via the aspiration manifold, and a second end for connecting with the waste container 31. The aspiration manifold 35 may also selectively connect the third fluid pathway 33 with ambient air, i.e., atmosphere, via a fifth fluid pathway 39.

The fifth fluid pathway 39 may have a first end connected with the third fluid pathway 33 and a second end connected with a second console connector 40 of the cassette 24. The second end of the fifth fluid pathway, through the second console connector 40, is, when the cassette 24 is inserted in the console 22, may be connected with atmosphere via the aspiration manifold 35 as described in more detail below.

Figure 3:
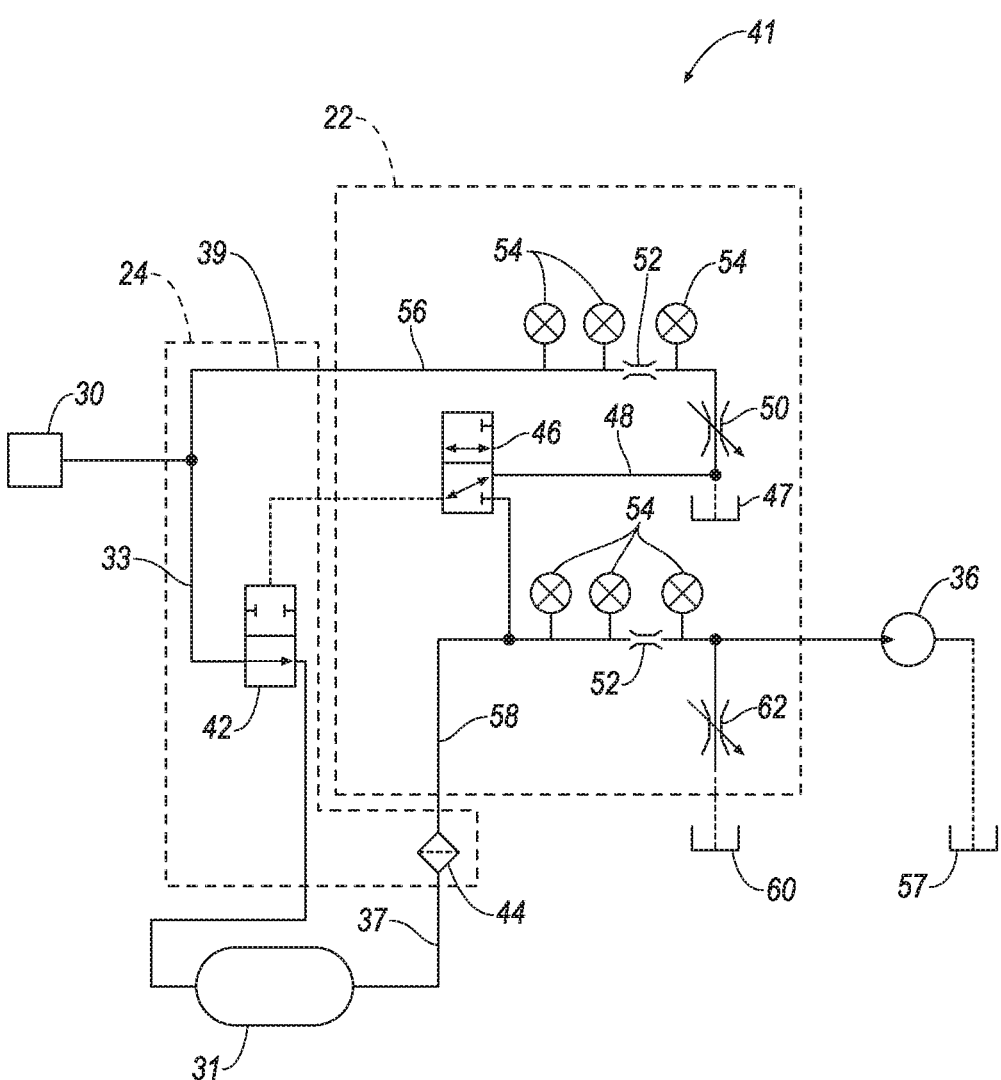
FIG. 3 is a schematic diagram of the surgical fluid management system of FIG. 2.

FIG. 3 schematically illustrates a suction portion 41 of the example fluid management system 20, that may in part compromise at least part of the aspiration manifold 35, at an example component level.

The cassette 24 may, as represented in FIG. 3 by the phantom line 24, include tubes, described in more detail below, with such tubes comprising at least portions of the fluid pathways 33, 37, 39 connecting the handpiece 30 and the canister 31 and the console 22, as represented by the phantom lines 22, and the vacuum source 36. The cassette 24 may also include a selectively actuable flow path restrictor that may be a flow restriction valve, which by way of example and not limitation may be a pinch valve 42, and a liquid stop connector 43. Alternatives to the pinch valve as the example selectively actuable flow restriction valve 42 include a gate valve that may be operated by an actuator, by way of example and not limitation, an electronic solenoid, an electronic stepper motor. The cassette 24 may also include a liquid-blocking filter 44. The liquid-blocking filter 44 may be disposed in the fourth fluid pathway 37 to prevent liquid in the canister 31 from reaching the console 22.

The restriction valve 42 may be used to restrict flow through the third fluid pathway 33, and thus restrict vacuum suction of the handpiece 30 at the surgical site and the removal of material therefrom. The restriction valve 42 may be at least in part pneumatically displaceable, and may alternatively include a valve actuator (not shown), that may comprise, by way of example and not limitation, a pneumatic piston-type valve actuator. The valve actuator may press a flexible tube 70, identified herein as a third tube 70, to pinch the tube 70 as described below. The tube 70 may comprise part of the third fluid pathway 33 responsive to atmospheric pressure or vacuum from a control valve 46. Such pinching of the pathway 33 may block flow through the third fluid pathway 33 between the handpiece 30 and the waste canister 31. The pinching may be effected by displacement of the piston-type valve actuator against the tube 70 responsive to an application of vacuum pressure to the valve actuator. The third tube 70 may serve as the valve 42, with the valve 42 being closed when the tube 70 is compressed by the valve actuator. The connection in FIG. 3 between valve 42 and valve 46 is shown as a broken, i.e., dashed, line to indicate that the actuator piston of the console 22 provides a mechanical connection between the console 22 and the third tube 70 of the cassette 24.

Such a valve actuator may be disposed in the console 22. Control of the restriction valve 42, by way of example and not limitation, achieved by selection of whether vacuum or atmospheric pressure is applied to the valve actuator to, respectively, close or open the restriction valve 42, may be effected by the control valve 46 that may be selectively displaced by a displacement actuator, by way of example and not limitation, comprising an electric solenoid (not shown). The control valve 46 and its associated displacement actuator may both be disposed in the console 22. The control valve 46, may, in a first position, the first position being an open position, connect the actuator piston of the restriction valve 42 to atmosphere via a first opening to atmosphere 47 via a connector path 48 for a rest position, displacing the valve 42 to an open position and allowing liquid to be communicated through the third fluid pathway 33. In a second position, the second position being a closed position, the control valve 46 may connect the actuator piston of the restriction valve 42 to the vacuum source 36, displacing the restriction valve 42 to the closed condition, and closing of the third fluid pathway 33. The restriction valve 42 is controlled by a selectively operated solenoid valve that, in a first mode, from the handpiece 30 to the canister 31. Selection between the pinched, i.e., closed position and the unpinched, i.e., open position, may be made by the system operator using a signaling device, by way of example and not limitation, a foot pedal (not shown) in communication with the console 22.

The fifth fluid pathway 39, connected on its first end to the third fluid pathway 33 between the restriction valve 42 and the handpiece 30, and on its second end to the second console connector 40, allows relief of vacuum at the surgical site via the console 22. A first variable flow vent valve 50 may be disposed in the console and may be used to connect the second end of the fifth fluid pathway 39 with atmosphere via the first opening to atmosphere 47. A combination of a defined flow path tube 52 and a plurality of, by way of example and not limitation, three, vacuum pressure sensors 54 may be disposed along a first vent fluid pathway 56 disposed in the console 22, between the cassette 24 and the vent valve 50, and may be used to estimate flow through the pathway 56. A console controller (not shown) may selectively open valve 50 to relieve vacuum in the third fluid pathway 33 responsive to vacuum measurements by sensors 54.

The fourth fluid pathway 37 may connect the canister 31 to the vacuum pump 36. The vacuum pump 36 may be connected to atmosphere via a second opening to atmosphere 57. The liquid-blocking filter 44 may be disposed in the fourth fluid pathway 37 to block liquid in the canister 31 from reaching the console 22. A vacuum communication fluid pathway 58 may be disposed in the console 22 between the vacuum source 36 and the cassette 24. A combination of a defined flow path tube 52 and a plurality of, by way of example and not limitation, three, vacuum pressure sensors 54 may be disposed along the vacuum communication fluid pathway 58 and may be used to estimate flow through the pathway 58. The vacuum communication fluid pathway 58 may also be connected to atmosphere via a third opening to atmosphere 60 through a second variable flow vent valve 62.

Figure 4:
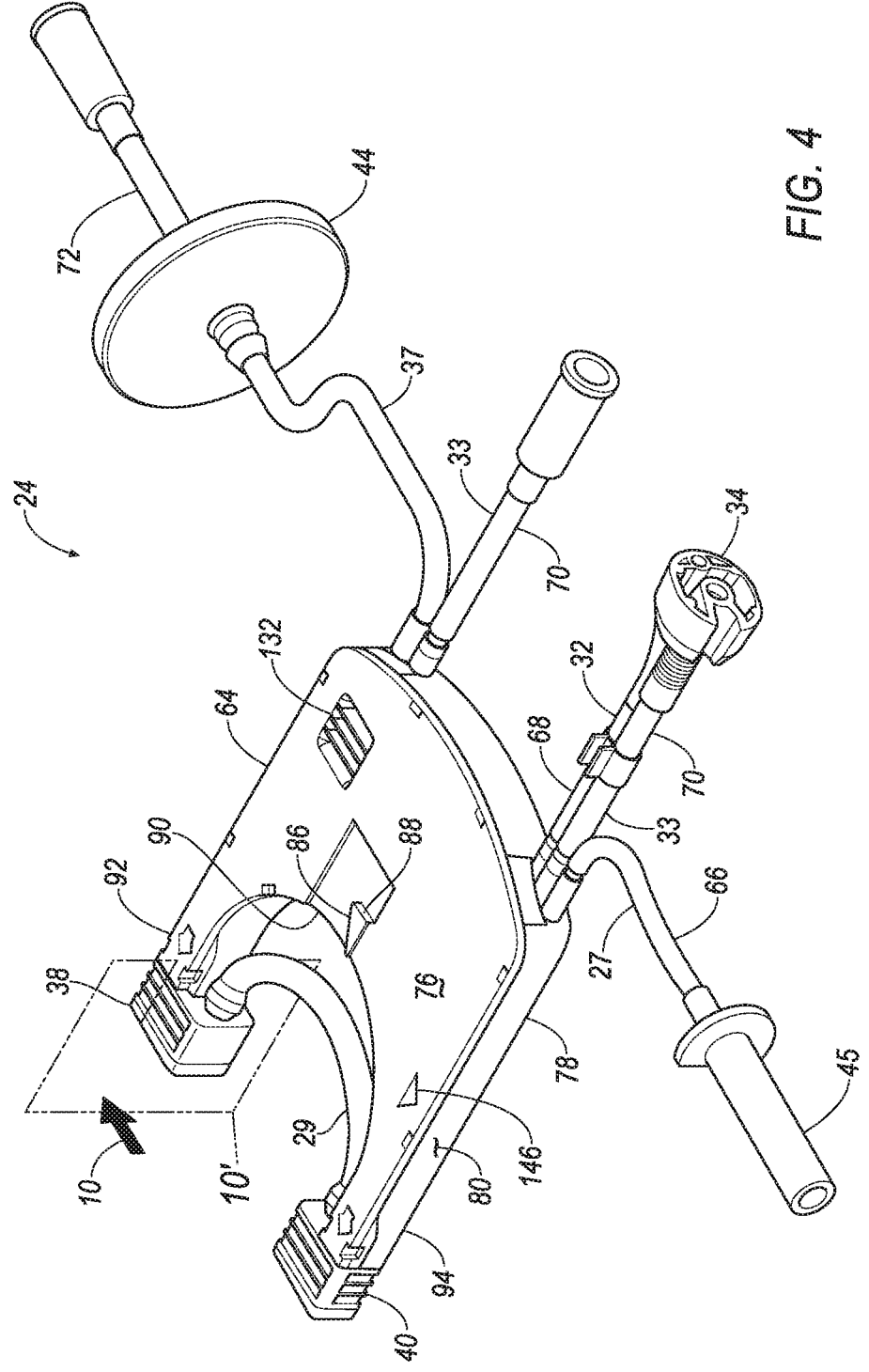
FIG. 4 is a perspective view of the cassette of FIG. 1.
Figure 5:
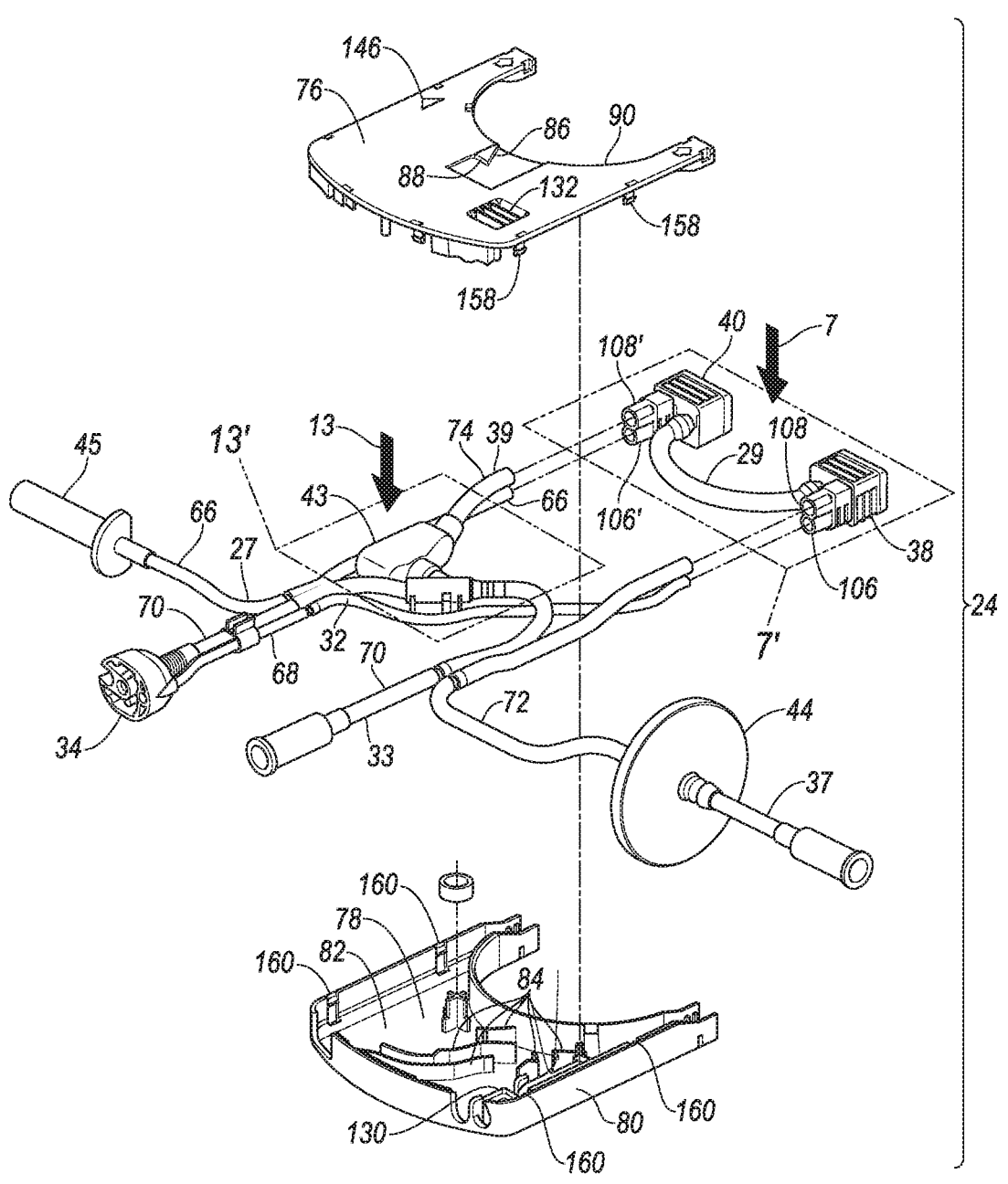
FIG. 5 is an exploded view of the cassette of FIG. 1.

The example cassette 24, as illustrated in FIG. 4 and in FIG. 5, includes a cassette housing 64, a liquid pump element, by way of example and not limitation, the compressible peristaltic pump tube 29, a first tube 66 that may comprise part of the first fluid pathway 27, a second tube 68 that may comprise part of the second fluid pathway 32, the third tube 70 that may comprise part of the third fluid pathway 33, a fourth tube 72 that may comprise part of the fourth fluid pathway 37, a fifth tube 74 that may comprise part of the fifth fluid pathway 39, the liquid stop connector 43, the first console connector 38 and the second console connector 40 and the liquid-blocking filter 44.

The fluid pathway tubes 66, 68, 70, 72, 74 and the peristaltic pump tube 29 may be flexible and transparent. One example material that may be used for the tubes 66, 68, 70, 72, 74 and 29 is Tygon® tubing. Each of the tubes 66, 68, 70, 72, 74, as suggested by the figures, need not be a continuous single piece of tubing, and may be spliced to join several smaller pieces of tubing to form any of the tubes 66, 68, 70, 72, 74.

The cassette housing 64, best shown in FIGS. 1, 4 and 5, is substantially rigid and may be formed of a plastic, by way of example and not limitation, a thermoset plastic. The example housing 64 may include a first wall 76 and a second wall 78 joined by a third, peripheral, wall 80 that spaces the first and second walls 76, 78 apart, defining an interior region 82 of the housing 64. A plurality of internal support walls 84 may be disposed within the housing 64. The internal support walls 84 aid in defining paths inside the housing 64 for the tubes 66, 68, 70, 72, 74. The fluid pathways 27, 32, 33, 37, 39 may alternatively be formed at least in part integrally with the housing 64, with molded chambers comprising portions of the pathways 27, 32, 33, 37, 39.

The housing 64 may include a retention barb 86 that may be molded into the first wall 76 of the housing 64, as best seen in FIG. 4. The barb 86 may be engaged on a latch engagement surface 88 by a latch (not shown) disposed inside the console 22. The latch may be manually released, or may be electrically released, depending on how the console 22 is configured, allowing the cassette 24 to be withdrawn from the console 22. An automatic electrically actuated latch release may be combined with an automatic cassette ejection system in the console in which the cassette 24 may be selectively pushed at least partially out of the console by an electric actuator, by way of example and not limitation, a solenoid or a motor.

The housing 64 may include a C-shaped side 90 cooperatively defined by the walls 76, 78, 80. The C-shaped side 90 may define a first arm, alternatively identified herein as a lower arm 92 and a second arm, alternatively identified herein as an upper arm 94. The first console connector 38 may be disposed at an end of the first arm 92. The second console connector 40 may be disposed at an end of the second arm 94. The console connectors 38, 40 comprise part of the housing 64, independent of whether the console connectors 38, 40 are formed separately from the walls 76, 78, 80 or integrally with the walls 76, 78, 80.

Figure 6:
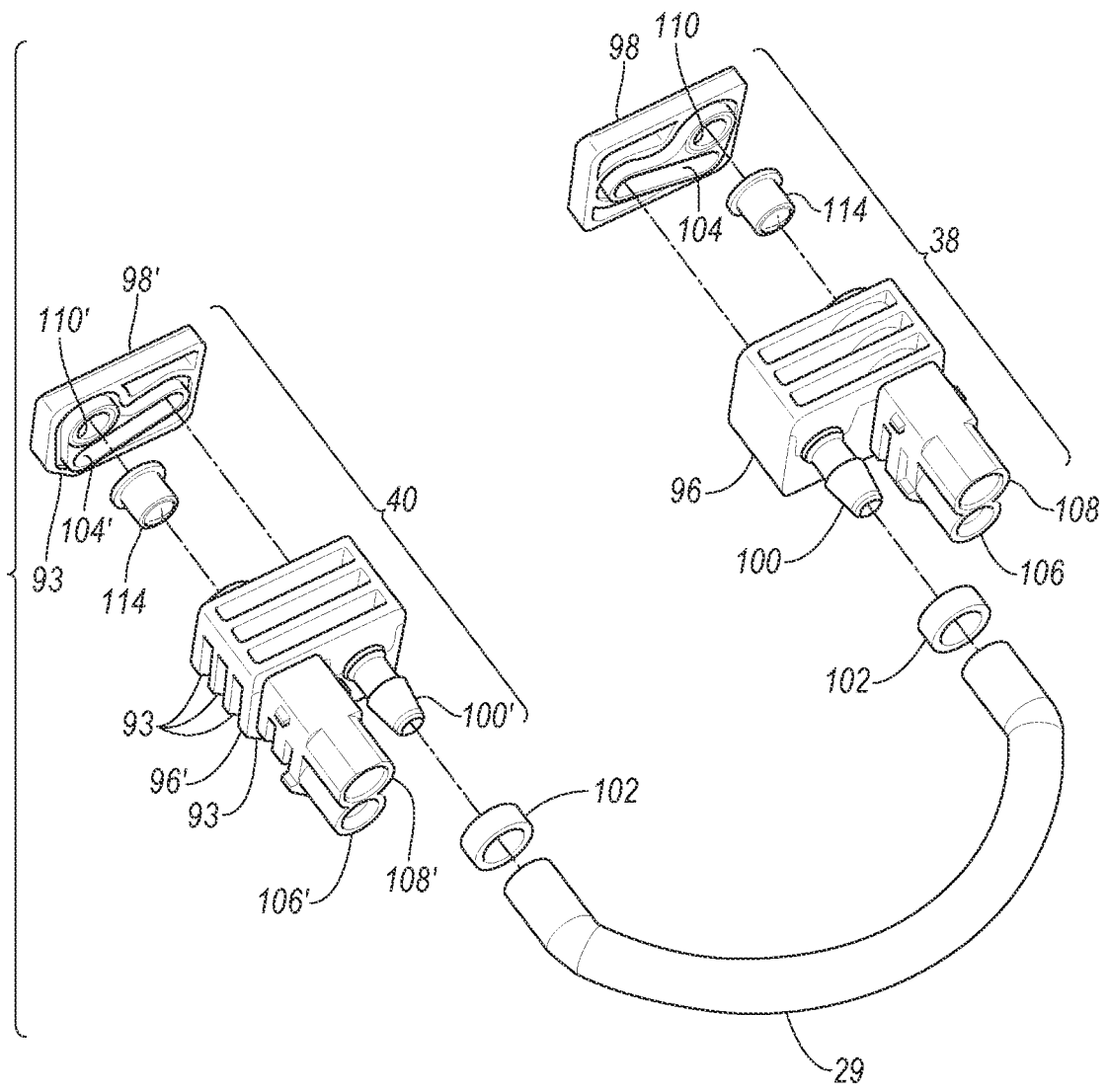
FIG. 6 is an exploded view of an example peristaltic pump tube and console connectors of the cassette of FIG. 1.
Figure 7:
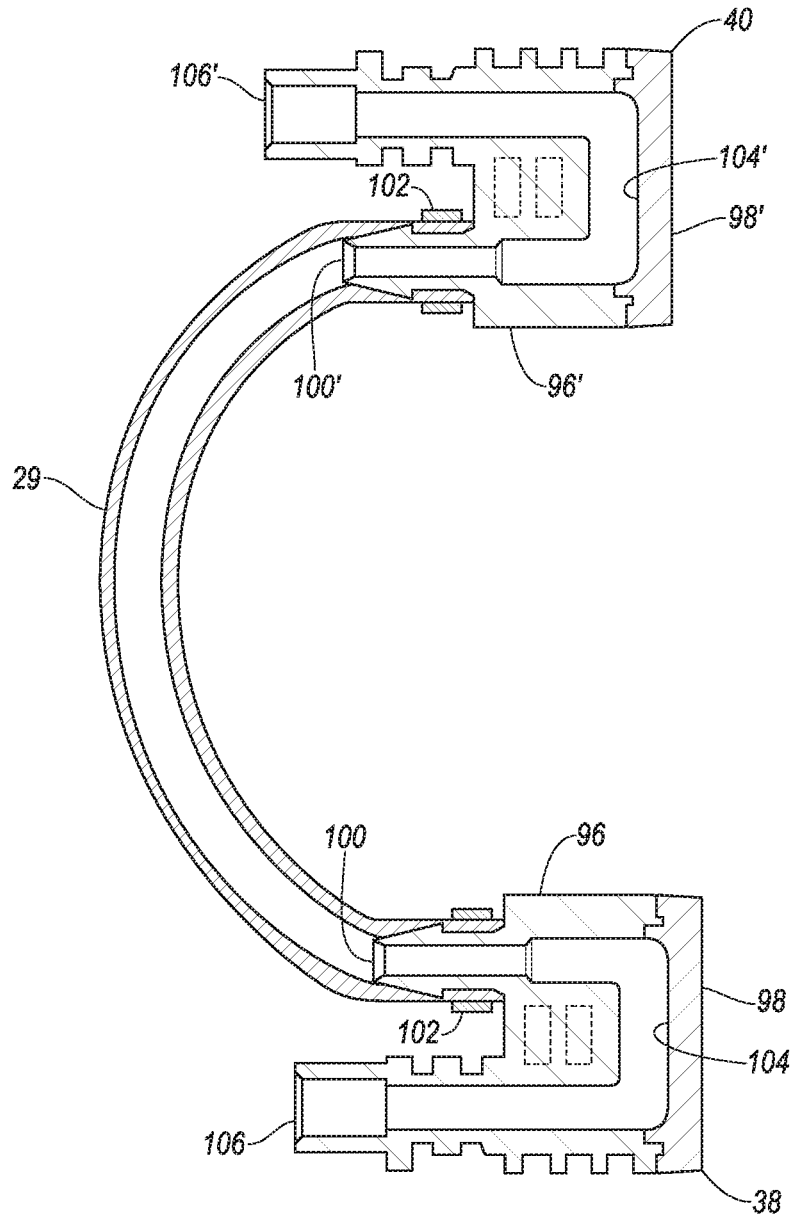
FIG. 7 is a sectional view of the tube and connectors of FIGS. 5 and 6, taken in the direction of arrow 7 through plane 7'.

The first and second console connectors 38, 40 shown in FIG. 5 as may be assembled to the peristaltic pump tube 29, are shown in the exploded view of FIG. 6. The console connectors 38, 40 may be substantially a mirror image of each other. The connectors 38, 40 may be additionally distinguished from each other with the provision of a cassette chamfer 93 along a corner edge of one of the connectors, by way of example and not limitation, the second connector 40. The chamfer 93 may serve as a keying feature, that is, an orientation feature of the cassette 24. Providing the console receiving slot 25 with a slot chamfer 95 complementary to the cassette chamfer 93 prevents insertion of the cassette 24 into the slot 25 in an incorrect, by way of example and not limitation, upside down, orientation. The cassette chamfer 93 may extend for a length of the cassette housing 64 as show in FIG. 1 to allow the cassette 24 to be received by the receiving slot 25. A cassette 24 that is alternatively configured to have an end of its housing 64 extend outside of the console 22 in an installed position may have the chamfer 93 extend less than a full length of the cassette housing 64. The console connectors 38, 40 except as noted, may be substantially rigid and may be formed of the same material as the cassette housing 64, by way of example and not limitation, a thermoplastic.

The first and second console connectors 38, 40 may respectively each include a first connector base 96 and a second connector base 96', and a first channel cap 98 and a second channel cap 98'. Each of the connector caps 98. 98' may be disposed over an end of the respective bases 96, 96'.

Figure 10:
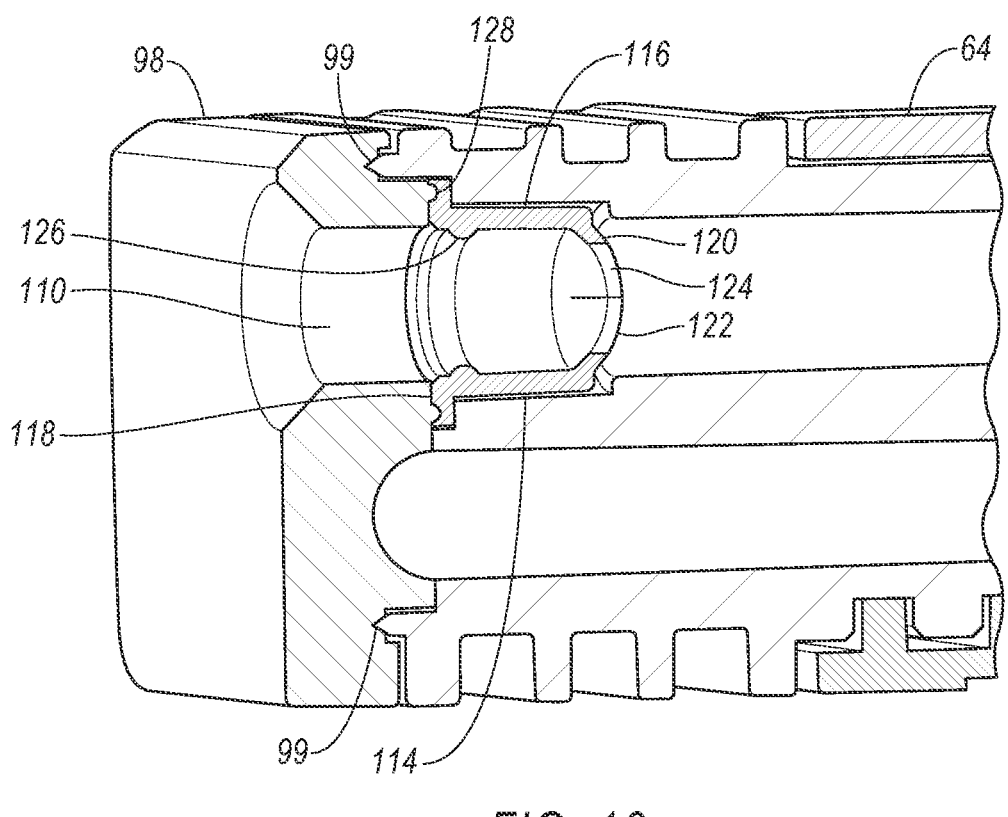
FIG. 10 is a sectional view of the console connector of FIG. 4 taken in the direction of arrow 10 through plane 10'.
Figure 11:
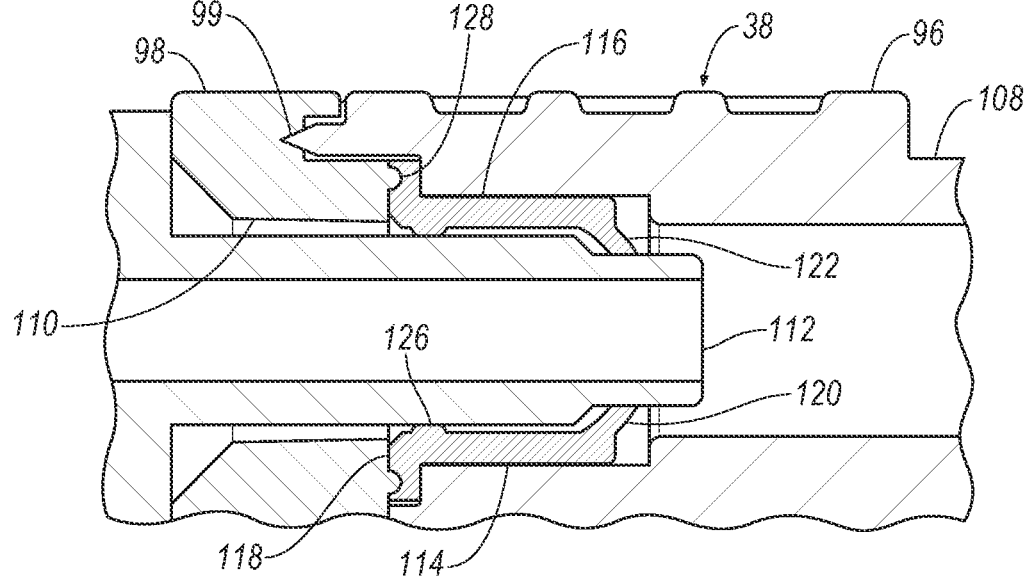
FIG. 11 is a sectional view of the console connector of FIG. 10 in receipt of a port tube.

The connector bases 96, 96' and the channel caps 98, 98' may be substantially rigid and may be formed of the same material as the cassette housing 64, by way of example and not limitation, a thermoplastic. After installation of a sealing valve 114, described in more detail below, the channel cap 98 may be fixed to the base 96 by any suitable joining means, by way of example and not limitation, adhesive bonding, press fit, welding. FIGS. 10 and 11 schematically illustrate an example ultrasonic weld 99 joining the cap 98 to the base 96 proximate to an outer periphery thereof. The base 96' and the cap 98' of the second connector 40 may be likewise joined to each other.

Each of the connector bases 96, 96' of the console connectors 38, 40 have a receiving tube, by way of example and not limitation, the example receiving tube being in the form of a barbed nipple 100 and 100' respectively. The nipple 100 of the first console connector 38 receives a first end of the peristaltic pump tube 29. The nipple 100' of the second console connector 40 receives a second end of the peristaltic pump tube 29. A retaining ring 102 may be slipped over the ends of the tube 29 to help retain the tube 29 on the nipples 100, 100'. As best shown in FIG. 1, the peristaltic tube 29 may be substantially parallel to the peripheral wall 80 of the C-shaped side 90.

The first channel cap 98 defines a connecting channel 104 of the first fluid pathway 27. The second channel cap 98' defines a connecting channel 104' of the second fluid pathway 32. While the sectional view of FIG. 7 suggests that the connecting channels 104 and 104' are coplanar with each other and the peristaltic pump tube 29, there may be an angular offset as suggested by the view of the channels 104, 104' in FIG. 6.

The first and second console connectors 38 and 40 may include each of a liquid interface sleeve 106 and 106' respectively and a pneumatic interface sleeve 108 and 108' respectively, each directed into the housing 64. The liquid interface sleeves 106, 106' and the pneumatic interface sleeves 108, 108' may be substantially the same and may differ principally in their use within the cassette 24.

The first and second console connectors 38 and 40 each have an aperture, by way of example and not limitation, a first pneumatic connector port 110 and a second pneumatic connector port 110', through their respective caps 98, 98'. The ports 110, 110' may be in alignment with the pneumatic interface sleeves 108, 108' to facilitate receipt of port tubes of the console 22, including a first pneumatic port tube 112 best shown in FIG. 11. Only the first pneumatic port tube 112 received by the first pneumatic connector port 110 is illustrated, as the relationship of a second pneumatic port tube (not shown) that would be received by the second pneumatic connector port 110' is substantially identical. The port tubes 112 define pneumatic console ports 112 of the console 22.

Figure 8:
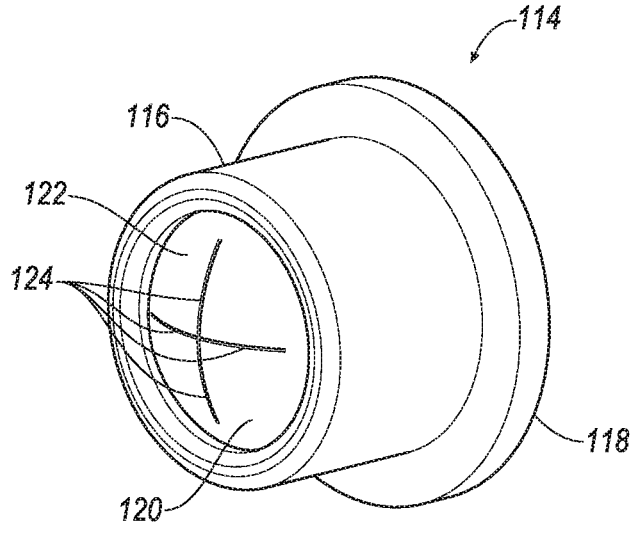
FIG. 8 is a first perspective view of a combined seal and valve of the connectors of FIGS. 6 and 7.
Figure 9:
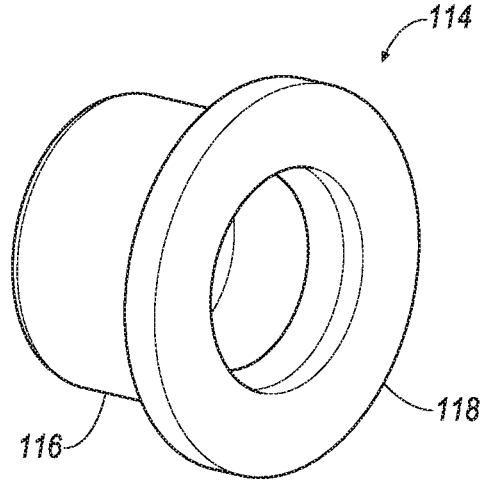
FIG. 9 is a second perspective view of the combined seal and valve of FIG. 8.

The sealing valve 114 may be captured between the cap 98 and the base 96. The sealing valve 114 may be formed of a flexible material well suited for use as a seal, by way of example and not limitation, any polymeric material, including by way of example and without limitation rubber and neoprene. As best shown in FIGS. 8 and 9, the sealing valve has cylindrical valve wall 116 of a first inside diameter that may be larger in diameter than an outer diameter the port tube 112. At an entry end of the cylindrical valve wall 116 is an annular seal 118 that may be formed integrally with the cylindrical valve wall 116. The annular seal 118 extends radially beyond the cylindrical valve wall 116.

A bidirectional valve 120 that may also be formed integrally with the cylindrical valve wall 116 is provided at a terminus end of the valve wall 116, opposite the entry end.

The valve 120 is in the form of a closure 122 over the terminus end. The closure 122 has a domed shape, in that the closure 122 forms a dome. The closure 122, in its dome, has a concave shape that is concave from inside the cylindrical valve wall 116, as viewed from the exterior of the cassette housing 64. The shape of the closure 122, while domed, may be less than a full hemisphere. The domed closure 122 has a plurality of, by way of example and not limitation, four, evenly spaced slits 124 radiating out from a center point and passing entirely through the closure 122. The number of slits 124 may be varied. The radial lengths of the slits 124 may be sufficient to allow the closure 122 to deflect and the port tube 112 to pass through the closure 122 without tearing the sealing valve 114. The concave domed shape of the valve 114 may aid in retaining any liquid that has reached the fourth and fifth tubes 72, 74 connected to the pneumatic connector ports 110, 110′ in the cassette 24. The valve 114 may operate as a bidirectional valve.

The sealing valve 114 may also include a lip 126 on an inside diameter of the cylindrical valve wall 116 and proximate to the entry end. An inside diameter of the lip 126 may be smaller than the outside diameter of the port tube 112. The lip 126 may be a pneumatic seal that seals against the port tube 112 to allow pneumatic sealing engagement therebetween. A bead 128 may be formed on the cap 98 encircling the port 110 on a side of the cap engaging the seal 118 to encourage sealing engagement therebetween.

The housing 64 may include a pinch-valve window 130 in the second wall 78 to accommodate the action of the actuator, by way of example and not limitation, the pneumatic piston that may be disposed in the console 22. The window 130 is aligned with the third tube 70. The housing 64 may also include a back-up base 132 in the first wall 176 in alignment with the window 130. The back-up base may provide a reaction surface allowing the compression, and thus the pinching, of the tube 70 by the pneumatic piston of the console 22.

Figure 12:
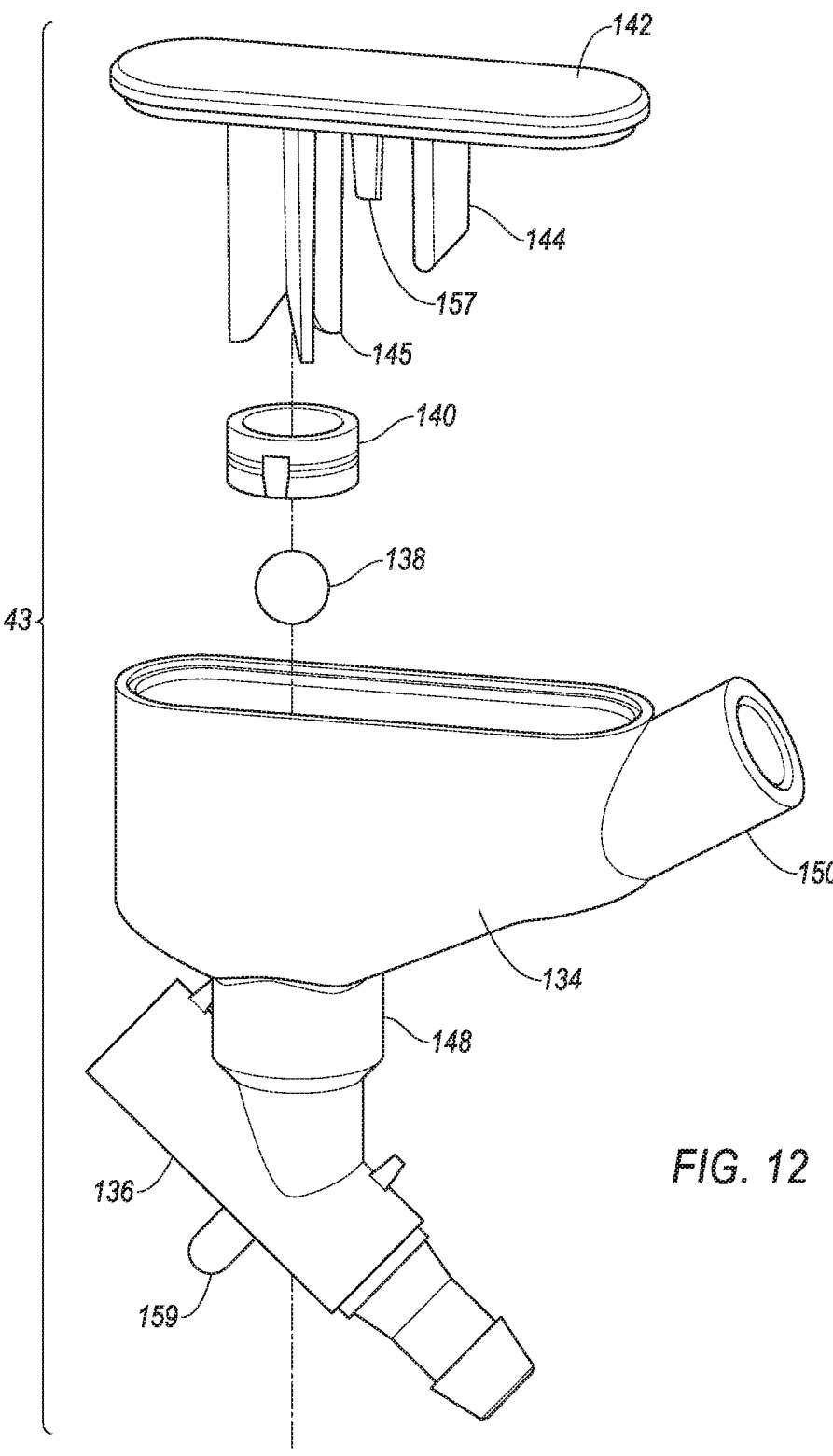
FIG. 12 is an exploded view of a vacuum regulation connector of the cassette.
Figure 13:
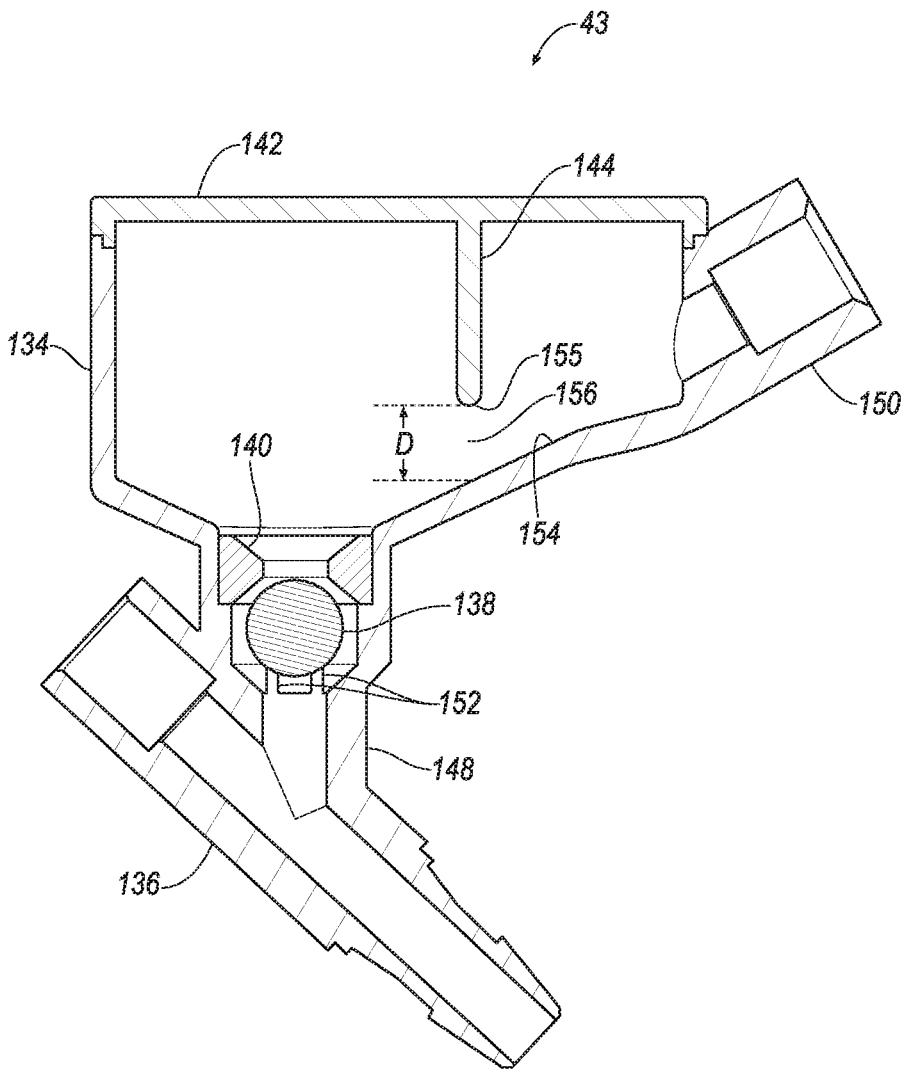
FIG. 13 is a sectional view of the vacuum regulation connector of FIG. 12 in the direction of arrow 13 through plane 13' of FIG. 5 with a check valve in an open position.
Figure 14:
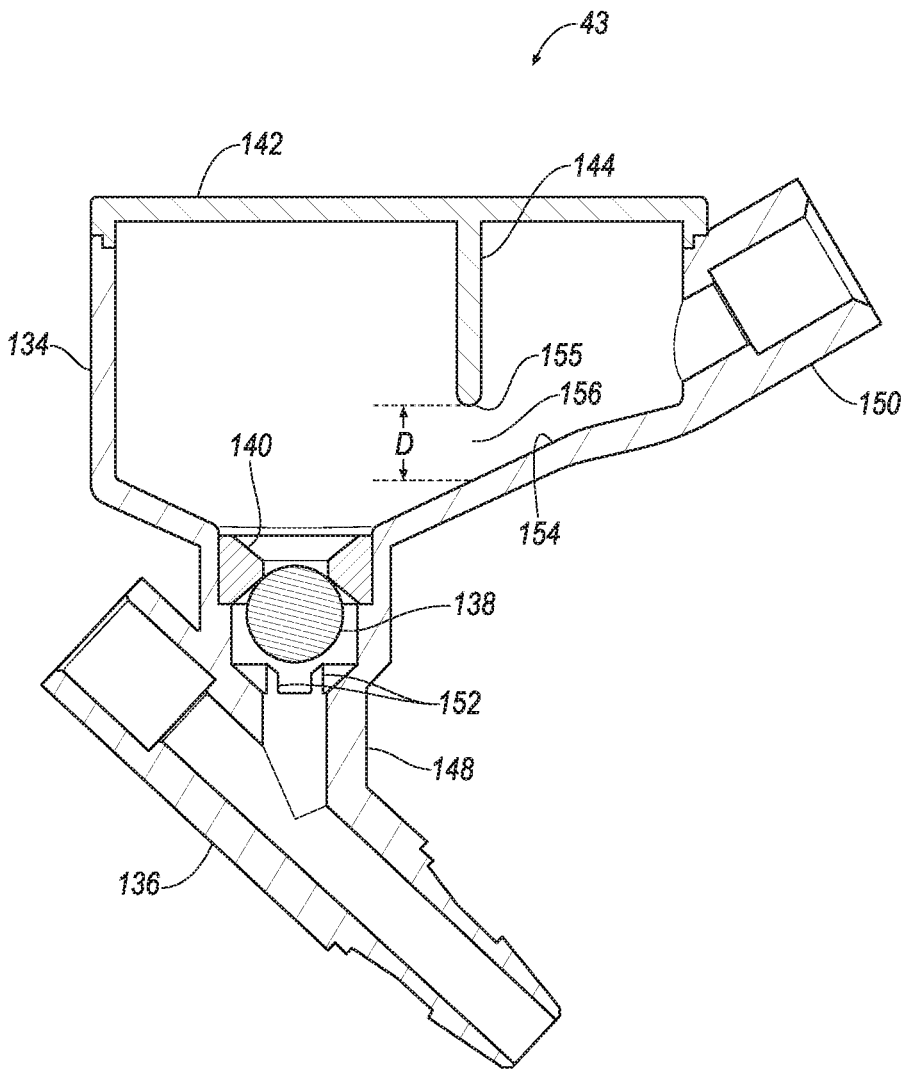
FIG. 14 is a sectional view of the vacuum regulation connector of FIG. 13 with a check valve in a closed position.

The liquid stop connector 43 is best illustrated in FIGS. 12, 13 and 14. The liquid stop connector includes a retention chamber 134, a pipe 136, a valve ball 138, a ball trap ring 140, a chamber cover 142, and a chamber baffle wall 144. The retention chamber 134 is alternatively referenced to herein as the reservoir 134.

The liquid stop connector 43 may be disposed between the fifth tube 74 and the third tube 70. The pipe 136 is disposed in the third tube 70. In an installed operating position, i.e., when the cassette 24 is installed in the console in an installed orientation consistent with a directional arrow 146 that may be molded into the housing 64, the chamber 134 is disposed above the pipe 136. The pipe 136 and the chamber 134 are fluidly connected by a first stem 148 connecting the pipe 136 with a bottom of the chamber 134. A second stem 150, near a top of the chamber and above the bottom of the chamber, fluidly connects the chamber 134 to the fifth tube 74. The chamber 134, the pipe 136, the first stem 148, and the second stem 150 may be integrally formed as a single piece of a common material. The chamber cover 142 is sealingly fixed to a top of the chamber 134. The valve ball 138 may be formed of a material that is light, flexible, and water resistant, one example material being silicone, for the purpose of promoting sealing between the ball 138 and the ring 140 responsive to either a liquid intrusion into the chamber from the third tube 70 and impingement thereagainst, or a rapid, that is, a sharp, change in relative pressure in the fifth tube 74 relative to the pressure in the third tube 70. The first stem 148 may have a plurality of support stakes 152 to support the ball 138 from below with restricting a return of fluid from the chamber to the pipe 136 and the third tube 70. In the open position, the ball is biased by gravity to rest against the support stakes 152. A bottom surface 154 of the chamber 134, alternatively identified as a floor 154 of the chamber 134, may be angled, that is, may taper towards the first stem 148 and the valve to facility drainage into the stem 148. The ball trap ring 140 is disposed over the ball 138. The ball trap ring 140 may be chamfered on a side facing the ball 138. Upward displacement of the ball 138, as may occur with entry of fluid into the first stem 148, presses the ball 138 against the concave surface of the trap ring 140, sealing against entry of fluid into the chamber 134 from the first stem 148. Collectively, the ball 138 and the trap ring 140 comprise a one-way ball-check valve.

The cover 142 may be formed integrally with the chamber baffle wall 144. The wall 142 may be in engagement with and may extend substantially vertically and downwardly from the cover 142. The baffle wall 144 is located between the first stem 148 and the second stem 150. A bottom edge 155 of the wall 144 may be spaced predetermined distance D from the bottom surface 154 of the chamber to provide a liquid return gap 156. The baffle wall 144 may have alternative configurations. For example, the baffle wall 144 may be formed as part of the chamber 134 and may extent from the floor 154 of the chamber 134 and extend laterally over, and above, the valve ball 138 and the ring 140.

The cover 142 may have a ball lock stop 145 extending from the cover 142. The ball lock stop 145, best shown in FIG. 12, extends downwardly from the cover 142. When the liquid stop connector 43 is assembled and in an installed orientation, the ball lock stop 145 may be disposed over the ball 138 and the ring 140. The ball lock stop 145, when employed, aids in retaining the ring 140 in an installed position in the first stem 148 of the liquid stop connector 43, the installed position best illustrated in FIGS. 13 and 14. The ball lock stop 145 is not shown in FIGS. 13 and 14 so as to better highlight the benefits of the baffle wall 144 in restricting unwanted fluid flow.

The cover 142 and the pipe 136 may each include a gate tab 157 and 159 respectively, as best shown in FIG. 12. The gate tabs 157, 159 may facilitate molding of each of the cover 142 and the integral chamber 134, pipe 136, first stem 148, and second stem 150.

The ball 138 is shown in a sealing position in FIG. 14 and an open position in FIG. 13.

The cassette 24 may be configured to encourage just a single use of the cassette 24 as one approach to addressing contamination of the cassette that occurs with use. Any reuse of the cassette 24 requires reconstruction of the cassette, requiring at a minimum, an opening up of the housing 64 and replacement of the fluid pathways, the seals and the valves in comprising the cassette 24. Barbed tabs 158 may be incorporated into at least one of the walls 76, 78, 80 for engagement with notches 160 on another of the walls 76, 78, 80 to both facilitate assembly of the housing 64 and to discourage disassembly of the housing 64. The single use of the cassette 24 may be further encouraged with the incorporation of a radio frequency identification ("RFID") tag (not shown) in the cassette housing 64, in combination with an RFID reader (not shown) in the console 22. One way to implement the use of an RFID tag and an RFID reader to aid in avoiding reuse of a single use component, in other words a disposable component, is described in US Patent Application Publication No. US20070085686A1, published on Apr. 19, 2007.

In operation, the cassette housing 24 may be pushed by the operator or an assistant which for example may include by way of example a nurse or a surgical technician, into the slot 25 of the console 22. Pressing the cassette housing 24 into the slot 25 causes the console's 22 first pneumatic port tube 112 and second pneumatic port tube (not shown) to be inserted into, respectively, the pneumatic connector port 110 of the first console connector 38 and the pneumatic connector port 110' of the second console connector 40 for engagement with the sealing valve 114 of each of the console connectors 38 and 40. Insertion of the first pneumatic port tube 112 into the first pneumatic connector port 110 connects the fourth tube 72 with the vacuum source 36. Similarly, insertion of the second pneumatic port tube (not shown) into the second pneumatic connector port 110' connects the fifth tube 74 with the aspiration manifold 35. If not integral with the console 22, the vacuum source 36 may be connected with the console 22 by the operator. The operator may also connect the IV bag connector 45 to the IV bag 26, connect the third tube 70 on one end to the canister 31 and on another end to the handpiece 30, and connect the fourth tube 72 with the canister 31. The operator may also connect the handpiece 30 with the second tube 68. Connecting the handpiece 30 with each of the second tube 68 and the third tube 70 may be achieved by use of the handpiece connector 34. The retention barb 86 of the cassette housing 64 may be engaged on its latch engagement surface 88 by the latch (not shown) disposed inside the console 22 to aid in retaining the cassette housing 64 in the console 22. The RFID tag in the cassette housing 64 may be recognized by the reader in the console 22 as identifying a new and appropriate cassette, allowing actuation of a full complement of the features of the fluid management system 20.

Once installed, the cassette 24 may be used to aid in both supplying liquid, by way of example and not limitation, sterile saline wash liquid ("the wash liquid"), from the IV bag 26 to a surgical site, and to remove waste liquid and surgical debris ("the waste") from the surgical site to the canister 31.

Upon selective demand from the operator, as may be indicated by a wash signaling device, by way of example and not limitation, a hand or foot operated wash switch (not shown), liquid may be drawn from the IV bag 26 and through the first tube 66 by the pump 28. The pump roller 21 may engage, that is, press against, the peristaltic pump tube 29, and, driven by the motor 23, displace the wash liquid through the peristaltic pump tube 29, from the second connector 40 to the first connector 38. The wash liquid then travels through the second tube 68, through the handpiece connector 34 and the handpiece 30 and to the surgical site.

The waste, upon selective demand from the operator, as may be indicated by a suction signaling device, by way of example and not limitation, a hand or foot operated suction switch (not shown), may be drawn from the surgical site, through the handpiece 30, through the handpiece connector 34, and through the third tube 70 and into the canister 31 by a negative pressure in the canister 31.

The vacuum in the canister 31 may be established by the vacuum pump 36, and communicating the negative pressure developed by the vacuum pump 36 through the manifold 35 that connects to the first pneumatic port tube 112, through the first connector 38, and through the fourth tube 72 to the canister 31.

An application of vacuum pressure at the handpiece 30 may be regulated, by way of example and not limitation, applied or relieved, by closing or opening the pinch valve 42. With the valve 42 in an open position, i.e., with the third tube 70 being unpinched, the vacuum in the canister 31 may be communicated to the handpiece via the third tube 70 to draw the waste from the surgical site. With the valve 42 in a closed position, as may be achieved with the third tube pinched by the valve actuator (not shown) in the console 22, flow through the third tube 70 is interrupted, and waste is not withdrawn from the surgical site. Such vacuum regulation may be achieved selectively by the operator with the use of the suction signaling device.

Vacuum at the handpiece 30 may be further regulated by regulation of the pressure in the third tube 70. Such regulation may be achieved by opening and closing the first variable flow vent valve 50. For example, the valve 50 may be opened to atmosphere to decrease the vacuum in the third tube 70 and at the handpiece 30 responsive to sensing of a predetermined magnitude of negative pressure at the handpiece 30 as may be indicated by one or more of the sensors 54 and as may be mandated by control logic disposed in the control console 22. Such regulation may be managed automatically by a controller (not shown) disposed in the console 22.

Upon completion of a procedure, the cassette 24 may be selectively ejected from the console 22 upon a command from the operator or an assistant, by way of example and not limitation, a command including pressing a button or otherwise signaling the console 22. The cassette 24 may be disposed of after its removal from the console 22 and after it has been disconnected from the IV bag 26, the canister 31 and the handpiece 30.

In the drawings, the same reference numbers indicate the same elements. Further, some or all of these elements could be changed. For example, the housing 64 may be cylindrical in shape, with a circular cross section rather than a rectangular cross section. Such a cassette may be received by a console having a cassette aperture of complementary cylindrical shape. Tabs could be provided on one of the housing or a wall inside the cassette aperture with receiving groove on the other to facilitate and twist and lock arrangement. Ports and seals in the walls of the cylinder and the opening may be aligned in a locked position to allow fluid connections. Alternative to ports and seals in the walls, a port tube concentric with the opening may be received by a port aperture in the housing. With regard to the processes, systems, methods, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claims.

Accordingly, it is to be understood that the above description is intended to be illustrative and not restrictive. Many embodiments and applications other than the examples provided would be apparent upon reading the above description. The scope should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

As used herein, the adverb "substantially" means that a shape, structure, measurement, quantity, time, etc. may deviate from an exact described geometry, distance, measurement, quantity, time, etc., because of imperfections in materials, machining, manufacturing, transmission of data, computational speed, etc.

All terms used in the claims are intended to be given their ordinary meanings as understood by those knowledgeable in the technologies described herein unless an explicit indication to the contrary is made herein. In particular, use of the singular articles such as "a," "the," "said," etc. should be read to recite one or more of the indicated elements unless a claim recites an explicit limitation to the contrary.

The Abstract is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

The invention claimed is:

1. A surgical irrigation cassette comprising:
a substantially rigid cassette housing defining a chamber therein and a first console connector including a first pneumatic connector port;
a liquid transfer portion of a pump including an intake side of the pump and an output side of the pump; and
a plurality of fluid pathways disposed at least in part within the chamber, including:
a first fluid pathway including a first end connected with the intake side of the pump, and a second end for connecting with a supply fluid container;
a second fluid pathway including a first end connected with the output side of the pump, and a second end for connecting with a handpiece;
a third fluid pathway including a first end for connecting with the handpiece, and a second end for connecting with a waste container; and
a fourth fluid pathway including a first end connected with the first console connector, a second end for connecting with the waste container, and a liquid-blocking filter.

2. The surgical irrigation cassette of claim 1, wherein the housing includes a first wall and a substantially parallel second wall connected by a peripheral third wall.

3. The surgical irrigation cassette of claim 1, wherein the housing has a substantially C-shaped side defining a first arm and a second arm, the first console connector is fixed to the first arm, and a second console connector including a second pneumatic connector port is fixed to one of the first arm and the second arm.

4. The surgical irrigation cassette of claim 3, wherein the second console connector is fixed to the second arm.

5. A surgical irrigation cassette comprising:
a substantially rigid cassette housing defining a chamber therein and a first console connector including a first pneumatic connector port;
a liquid transfer portion of a pump including an intake side of the pump and an output side of the pump; and

a plurality of fluid pathways disposed at least in part within the chamber, including:
a first fluid pathway including a first end connected with the intake side of the pump, and a second end for connecting with a supply fluid container;
a second fluid pathway including a first end connected with the output side of the pump, and a second end for connecting with a handpiece;
a third fluid pathway including a first end for connecting with the handpiece, and a second end for connecting with a waste container; and
a fourth fluid pathway including a first end connected with the first console connector, and a second end for connecting with the waste container,
wherein the housing has a substantially C-shaped side defining a first arm and a second arm, the first console connector is fixed to the first arm, a second console connector including a second pneumatic connector port is fixed to one of the first arm and the second arm, the pneumatic connector ports are each defined by an associated aperture for receiving a port tube, and the console connectors further each includes a seal for sealing engagement with the port tube.

6. A surgical irrigation cassette comprising:
a substantially rigid cassette housing defining a chamber therein and a first console connector including a first pneumatic connector port;
a liquid transfer portion of a pump including an intake side of the pump and an output side of the pump; and
a plurality of fluid pathways disposed at least in part within the chamber, including:
a first fluid pathway including a first end connected with the intake side of the pump, and a second end for connecting with a supply fluid container;
a second fluid pathway including a first end connected with the output side of the pump, and a second end for connecting with a handpiece;
a third fluid pathway including a first end for connecting with the handpiece, and a second end for connecting with a waste container; and
a fourth fluid pathway including a first end connected with the first console connector, and a second end for connecting with the waste container,
wherein the housing has a substantially C-shaped side defining a first arm and a second arm, the first console connector is fixed to the first arm, a second console connector including a second pneumatic connector port is fixed to one of the first arm and the second arm, and the console connectors each includes a seal for pneumatic sealing engagement with a pneumatic port tube of a console.

7. The surgical irrigation cassette of claim 6, wherein each console connector includes a bidirectional valve having a closed condition when the console connectors are not in receipt of the pneumatic port tubes.

8. The surgical irrigation cassette of claim 7, wherein the bidirectional valve is formed of a polymeric material and the bidirectional valve includes a concave shape from an exterior orientation with slits therethrough.

9. The surgical irrigation cassette of claim 8, wherein the bidirectional valve and the seal are formed integrally of the polymeric material.

10. The surgical irrigation cassette of claim 1, wherein the housing includes a window disposed over one of the pathways for receiving a path restrictor.

11. The surgical irrigation cassette of claim 1, wherein the housing includes a window disposed over the third fluid pathway for receiving a path restrictor.

12. The surgical irrigation cassette of claim 1, further comprising a fifth fluid pathway that includes a first end connected with the third fluid pathway, and a second end connected with a second console connector of the housing.

13. A surgical irrigation cassette comprising:
a substantially rigid cassette housing defining a chamber therein and a first console connector including a first pneumatic connector port;
a liquid transfer portion of a pump including an intake side of the pump and an output side of the pump; and
a plurality of fluid pathways disposed at least in part within the chamber, including:
 a first fluid pathway including a first end connected with the intake side of the pump, and a second end for connecting with a supply fluid container;
 a second fluid pathway including a first end connected with the output side of the pump, and a second end for connecting with a handpiece;
 a third fluid pathway including a first end for connecting with the handpiece, and a second end for connecting with a waste container;
 a fourth fluid pathway including a first end connected with the first console connector, and a second end for connecting with the waste container; and
 a fifth fluid pathway including a first end connected with the third fluid pathway, and a second end connected with a second console connector of the housing; and
a liquid stop connector that comprises:
 a reservoir disposed in the housing between the third fluid pathway and the fifth fluid pathway; and
 a normally open one-way valve disposed between the third fluid pathway and the reservoir.

14. The surgical irrigation cassette of claim 13, further comprising a pipe disposed in and comprising part of the third fluid pathway, wherein the reservoir is disposed between the pipe and the fifth fluid pathway and the one-way valve is disposed between the pipe and the reservoir.

15. The surgical irrigation cassette of claim 13, wherein the one-way valve comprises a ball-check valve and wherein in an installed orientation a ball of the ball-check valve is biased to an open position by gravity and is forced upward to a closed position by one of impingement of liquid from the third fluid pathway thereagainst and an increase in fluid pressure in the third fluid pathway relative to the fifth fluid pathway.

16. The surgical irrigation cassette of claim 15, wherein the reservoir includes an angled floor above the ball-check valve tapering toward the ball-check valve, defining a liquid flow path in the installed orientation from the reservoir to the ball-check valve for flow therepast and into the third fluid pathway in the open position.

17. The surgical irrigation cassette of claim 16, wherein the reservoir includes a baffle wall horizontally positioned between the ball-check valve and a connection to the fifth fluid pathway.

18. The surgical irrigation cassette of claim 17, wherein the baffle wall has a lower end defining a liquid-return gap between the baffle wall and the floor and a top end in engagement with a cover of the reservoir.

19. The surgical irrigation cassette of claim 1, further including a handpiece connector connected to the second end of the second fluid pathway and the first end of the third fluid pathway, the handpiece connector comprising part of each of the second fluid pathway and the third fluid pathway.

20. The surgical irrigation cassette of claim 1, wherein the first fluid pathway includes an IV bag connector.

21. The surgical irrigation cassette of claim 1, wherein the liquid transfer portion of the pump comprises a compressible peristaltic pump tube disposed outside of the housing.

22. A surgical irrigation cassette comprising:
a substantially rigid cassette housing defining a chamber therein and a first console connector including a first pneumatic connector port;
a liquid transfer portion of a pump including an intake side of the pump and an output side of the pump, the liquid transfer portion of the pump comprising a compressible peristaltic pump tube disposed outside the housing;
a plurality of fluid pathways disposed at least in part within the chamber, including:
 a first fluid pathway including a first end connected with the intake side of the pump, and a second end for connecting with a supply fluid container;
 a second fluid pathway including a first end connected with the output side of the pump, and a second end for connecting with a handpiece;
 a third fluid pathway including a first end for connecting with the handpiece, and a second end for connecting with a waste container; and
 a fourth fluid pathway including a first end connected with the first console connector, and a second end for connecting with the waste container; and
a second console connector, wherein each of the console connectors includes:
 a substantially rigid connector housing having a receiving tube that is in engagement with the peristaltic pump tube with the receiving tube defining a part of one of the first fluid pathway and the second fluid pathway; and
 a pneumatic interface sleeve formed as part of the connector housing and having an aperture therethrough and a seal disposed in the aperture.

23. The surgical irrigation cassette of claim 22, further including in each console connector a bidirectional valve having a closed condition when the cassette is not disposed in a console.

24. The surgical irrigation cassette of claim 1, wherein the fluid pathways disposed within the housing comprise at least in part flexible tubes and the housing includes internal support walls along which the flexible tubes are disposed.

* * * * *